United States Patent [19]

Day

[11] Patent Number: 4,819,274
[45] Date of Patent: Apr. 11, 1989

[54] VISOR CAP WITH A DETACHABLE EYE SHIELD

[76] Inventor: Shenq T. Day, 1 Chung Yang North Road, Ching Shui, Taichung Hsien, Taiwan

[21] Appl. No.: 132,552

[22] Filed: Dec. 14, 1987

[51] Int. Cl.$^4$ ............................ A42B 1/20; A42B 1/24
[52] U.S. Cl. ............................................................ 2/10
[58] Field of Search ........................ 2/10, 199, 453, 12

[56] References Cited

U.S. PATENT DOCUMENTS

| | | | |
|---|---|---|---|
| 2,538,607 | 1/1951 | Vaca | 2/10 |
| 2,619,641 | 12/1952 | Vaca | 2/10 |
| 2,725,560 | 12/1955 | Feldman | 2/10 |

FOREIGN PATENT DOCUMENTS 1104655  6/1955  France ...................................... 2/10

*Primary Examiner*—Peter Nerbun
*Attorney, Agent, or Firm*—Wenderoth, Lind & Ponack

[57] ABSTRACT

A cap including a detachable eye shield adjustably mounted on a mounting block which is removably engaged in a dovetail groove formed on the central portion of the under side of the visor member of the cap. A shaft member disposed on the upper frame of the eye shield is pivotally snap-engaged in the holder portion of the mounting block whereby the eye shield can be raised up and down relative to the visor member. By pushing the mounting block back and forth along the dovetail groove the eye shield can be moved to adjust the distance relative to the eyes.

3 Claims, 2 Drawing Sheets

VISOR CAP WITH A DETACHABLE EYE SHIELD

BACKGROUND AND SUMMARY OF THE INVENTION

The present invention relates to a visor cap and, more particularly, to a visor cap mounted with a detachable and adjustable eye shield on the lower surface of the forwardly projecting visor member of a cap.

It is perhaps well known that many persons who perform outdoor activities use sunglasses or goggles for eye protection to avoid particulate matter from getting into the eyes and also wear a cap or hat with a visor for shading the eyes. An object of this invention is to provide a visor cap having on the bottom side of the visor member a detachable eye shield, such as a pair of sunglasses or wind-shield goggles, mounted by way of an attachment groove and a mounting block. The display aspect is considered by many to be a significant style feature.

In the past, a number of devices have been proposed for attaching eyeglasses to the visor of a cap, such as is disclosed in U.S. Pat. No. 4,541,125 in which a clip part attaches the main eyeglasses part to a cap visor whereby the eyeglasses part is pivotally movable between operative and inoperative positions. Other types of devices have been utilized for attaching eyeglasses or an eye shield to a cap such as that disclosed in U.S. Pat. Nos. 4,304,005 and 4,636,048.

It is an object of the present invention to provide a visor cap comprising a mounting block that attaches the eye shield member to the visor member. By pushing the mounting block back and forth along the groove defined on the underside of the visor the eye shield can be moved to adjust the distance thereof from the eyes.

A further object of the present invention is to provide a visor cap in which a shaft member disposed on the mounting frame of the eye shield is pivotally snap-engaged in a holder portion of the mounting block permitting the eye shield to be changed from an up and down position relative to the visor member.

The foregoing objects and advantages of the present invention will be further appreciated from a consideration of the following detailed description and accompanying drawings.

DETAILED DESCRIPTION OF THE PREFERRED EMBODIMENT

Figure 1:
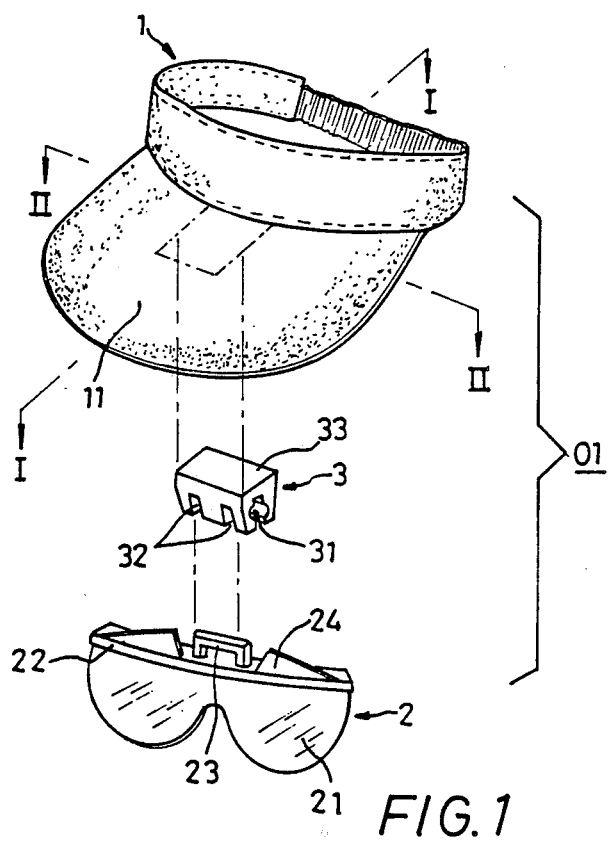
FIG. 1 is a perspective, exploded view of a visor cap constructed in accordance with the principle of the invention.
Figure 4:
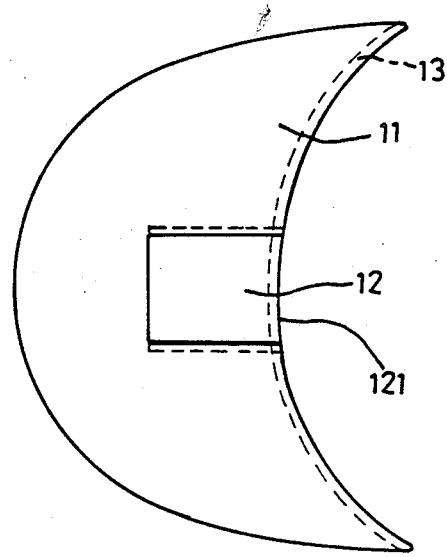
FIG. 4 is a bottom view of the visor member of the cap.

Referring now to FIGS. 1 through 4, the visor cap of the present invention, designated generally by the numeral 01, comprises a cap body 1 having at least a visor member 11, an eye shield member 2 and a mounting block 3.

The cap body 1 may be of any types of a cap having the forwardly projecting visor member 11 attached thereto and integrally formed of plastic. Adjacent the rear edge on the lower side middle portion of the visor member 11 is located a longitudinally directed dovetail groove 12 defining an entry port 121 at its rear side. The part of this attachment groove may also be formed as a separate member and next affixed to the underside surface of the visor member (not shown).

The eye shield member 2, such as sunglasses or wind-shield goggles, has a single piece wind-shield lens 21 and a mounting frame 22 having on its lower end a groove 25 for frictional attachment thereto of the upper end of the lens 21. This mounting frame 22 on the upper surface middle portion is provided with a transverse inverted C-shaped mounting shaft 23 formed integrally with the mounting frame 22. On either side of this mounting frame 22 are formed in a symmetrical manner a pair of triangular supplementary plates 24 to conform upwardly to the radian of the underside surface of the visor portion 11 and to extend to the respective outer terminal end. It should be noted that the transverse mounting shaft 23 may be formed directly across the two sides connecting the two opposite ends of the pair of the supplementary plates 24. Furthermore, the aforesaid mounting frame 22 having the mounting shaft 23 may also be integrally formed with the lens body 21 from a transparent plastic material.

Figure 2:
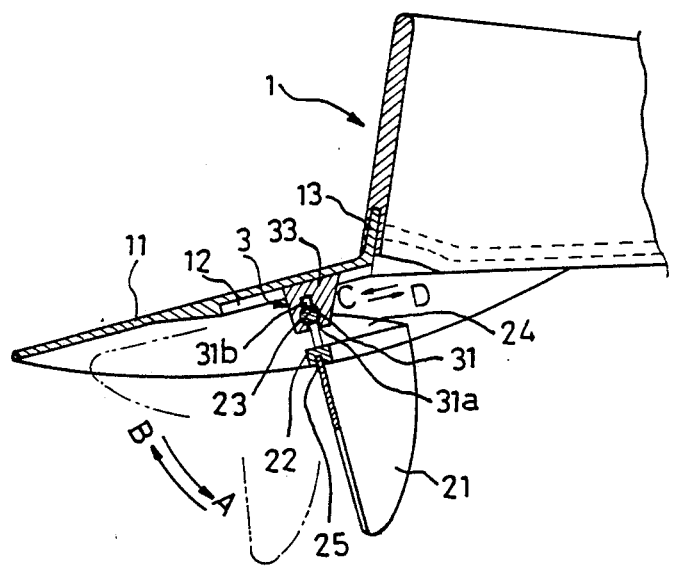
FIG. 2 is a longitudinal sectional view of the visor cap in the assembled state taken along the line II of FIG. 1.
Figure 3:
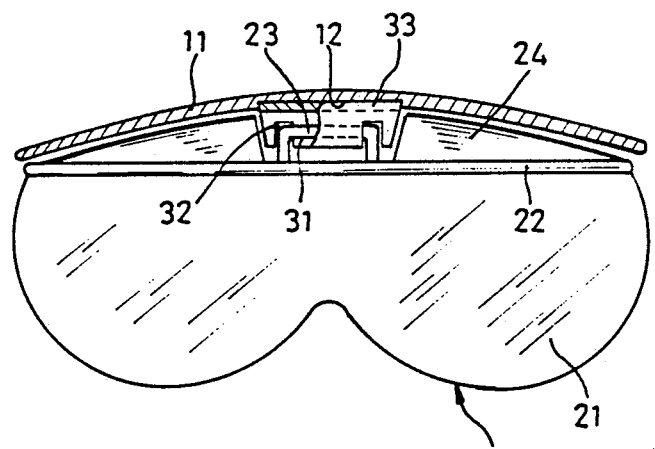
FIG. 3 is a transverse sectional view of the visor cap in the assembled state taken along the line I of FIG. 1.

The mounting block 3, as shown in FIGS. 1-3, is integrally molded from a synthetic resin material of a trapezoidal shape provided at the shorter-side end with a downwardly open retaining channel 31 having at the bottom part an opening 31a substantially narrower in width than the section of the mounting shaft 23 and at the center a cavity 31b adapted to hold and work resiliently with the mounting shaft 23 and a pair of similarly downwardly open transverse channels 32 arranged in transverse direction to the retaining channel 31 for rotating therein the legs of the mounting shaft. The broader-side end (i.e., the upper end in the drawings) of the mounting block 3 is so configured that the base 33 can be engaged frictionally and moved back and forth in the above-said groove 12. The mounting block 3 may also be formed in such a way that the mounting shaft 23 is pivotally accommodated in the mounting block 3 and the above-said transverse channels 32 together with the projecting portions on the lateral side walls thereof may thus be excluded.

It may be appreciated that by the mounting shaft 23 being held in the retaining channel 31 of the mounting block 3, the eye shield member 2 is frictionally disposed in the lower portion of said mounting block 3 and can thus be turned up and down in a direction as designated by arrows A and B shown in FIG. 2. Furthermore, since the base 33 of the mounting block 3 is removably attached in the dovetail groove 12 on the underside of the visor member 11, the eye shield member 2 can be adjusted in its position back and forth as well as up and down underneath the visor member 11 and is removably mountable thereto.

Again, since the eye shield member 2 is mounted by the mounting shaft 23 thereof in the retaining channel 31 of the mounting block 3, the frictional resistance developed therebetween will further enable the eye shield member 2 to be at any angle and still be held in position in the retaining chamber 31. The frictional surfaces may also be formed by the formation of several rows of radial toothed racks on the outer circumference of the mounting shaft 2 and the inner wall of the retaining channel 31.

With respect to the use and operating of the visor cap constructed in accordance with the instant invention, when it is desired that the eye shield member 2 be mounted on the cap body 1, the mounting block 3 is first attached by its base portion 33 to the groove 12 on the underside surface of the visor member 11 through the opening 121 located at the rear side of the groove 12. Following this arrangement, the mounting block 3 is now capable of being slid back and forth and to be engaged frictionally in the groove 12. The eye shield member 2 is next mounted by snapping in position the mounting shaft 23 thereof in the retaining channel 31 of the mounting block 3 whereby this mounting shaft 23 is held frictionally within the retaining channel 31 and is prevented by the relatively narrower-mouthed opening 31a from easily falling out.

In this arrangement, depending on the user's preference, the a user may turn the lens 21 of the eye shield member 2 downward in a direction as indicated by the arrow A in FIG. 3 to be in a substantially vertical position relative to the visor member 11 for use. While in this downward position of the lens 21, the eye shield member 2 together with the mounting block 3 disposed thereabove may also be moved back and forth in directions as indicated by arrows C and D in FIG. 3 to enable the wearer to appropriately adjust the distance between the lens 21 and the face. Again, when not in use, the lens 21 may be raised directly upwardly in direction as indicated by the arrow B in FIG. 3, thus permitting the lens 21 to abut against the underside of the visor member 11. If it is desires, the lens 21 may be separately disconnected and removed from the mounting block 3, or the lens 21 may also be detached together with the mounting block 3 from the visor member 11 so that the cap body 1 can be separately used while facilitating the eye shield member 2 to be kept separately.

From the foregoing, it is seen that the visor cap in accordance with the invention provides an eye shield which can be readily attached to the bottom surface of the visor through the intermediary of the mounting block. When mounted in position on the visor, the eye shield lens can also be conveniently and quickly detached from the user or when not in use the lens can be raised up to rest closely adjacent to the underside of the visor. The design and construction of the mounting block permits ready attachment and detachment of the eye shield to and from the visor, as well as ready attachment and detachment of the two parts relative to each other. The frictional engagement of the mounting block with the visor further allows the adjustment of distance to be made between the position of the eye shield and the eyes.

While a preferred embodiment in accordance with the present invention has been illustrated and described, it is understood that various modifications may be resorted to without departing from the spirit and scope of the appended claims.

I claim:

1. A visor cap having a detachable eye shield member, comprising:
    a cap body;
    a forwardly projecting visor member attached along the rear edge thereof to the cap body, said visor member having formed in the bottom surface thereof a dovetail shaped attachment groove extending in a longitudinal direction away from said cap body; and
    a mounting block engaged in said groove and movable along said groove, said mounting block having a mounting shaft detachably and pivotally mounted thereon and an eye shield member mounted on said mounting shaft for being raised up and down relative to said visor member on said shaft.

2. A visor cap as claimed in claim 1 in which said visor member is made of plastic and said dovetail groove is open at the end thereof adjacent said cap body, and said mounting block is formed of a synthetic resin material having a trapezoidal shape frictionally engaged in said dovetail groove.

3. A visor cap as claimed in claim 1 in which said mounting block has on the lower portion a transverse retaining channel having a downward opening substantially narrower in width than the cross-section of said mounting shaft and capable of being resiliently expandable, said mounting shaft being pivotally engageable in said retaining channel.

* * * * *